Figure 1:
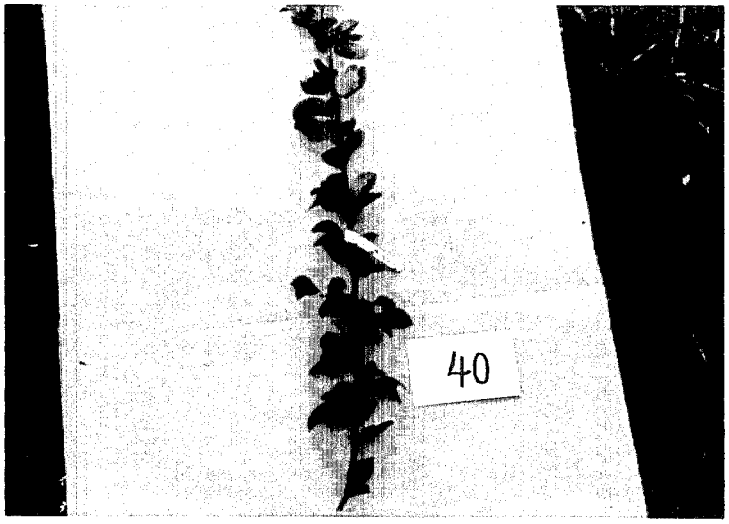
Figure 2:
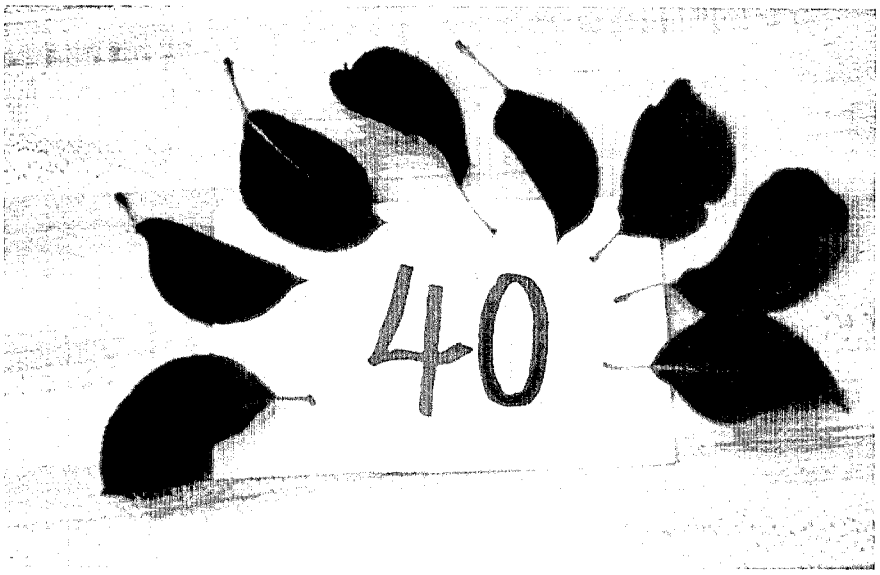
Figure 3:
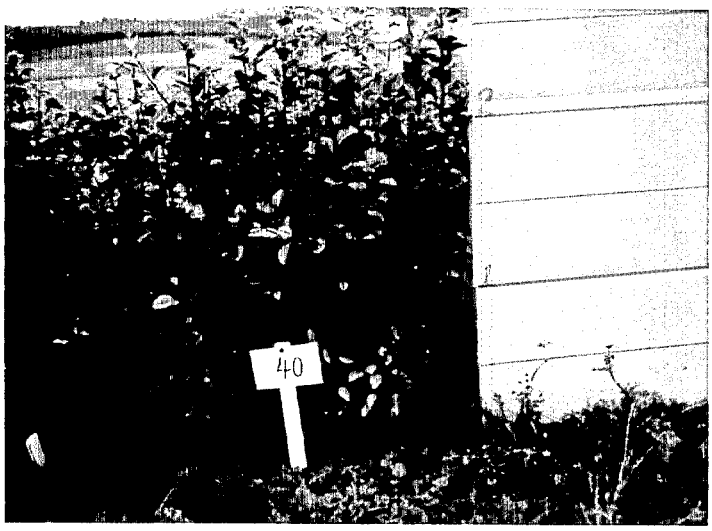
Figure 4:
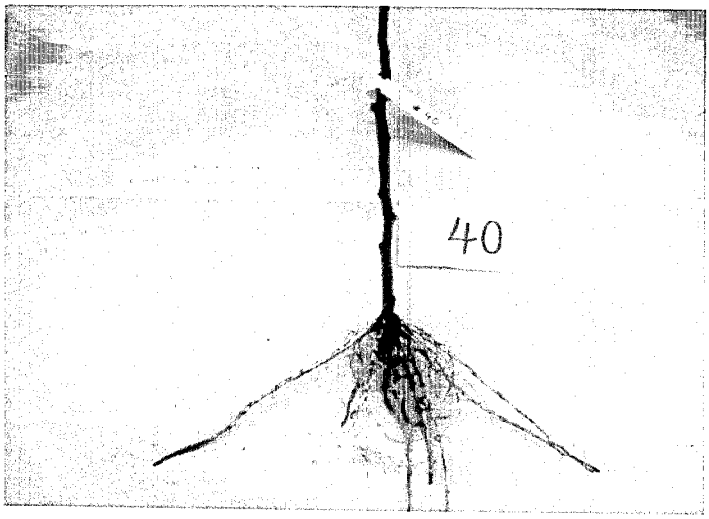

United States Patent [19]

Brooks

[11] Patent Number: Plant 5,412

[45] Date of Patent: Mar. 5, 1985

[54] PEAR TREE

[75] Inventor: Lyle A. Brooks, Forest Grove, Oreg.

[73] Assignee: Carlton Nursery Company, Inc., Dayton, Oreg.

[21] Appl. No.: 534,177

[22] Filed: Sep. 20, 1983

[51] Int. Cl.[3] ..... A01H 5/03

[52] U.S. Cl. ..... Plt./36

[58] Field of Search ..... Plt./36

*Primary Examiner*—Robert E. Bagwill

*Attorney, Agent, or Firm*—Harvey B. Jacobson; Clarence A. O'Brien

[57] ABSTRACT

This invention relates to a new and distinct variety of pear tree (Variety 40) which is useful as a size-controlling clonal pear rootstock. The new variety originated as a single seedling which was selected from a large group of pear seedlings which were grown from open-pollinated seed. This seed was harvested from Old Home pear trees (*Pyrus communis*) growing in an isolated planting with Farmingdale pollinizers.

Pear varieties grown on the understock of this new rootstock clone are approximately 65% of the size of like pear trees grown on Domestic Bartlett seedling rootstocks (*Pyrus communis*). This "dwarfing" selection can be easily increased by vegetative propagation methods; particularly by hard and softwood cuttings. It is graft-compatible with all major pear varieties. It was selected for its non-rootsuckering habit, its resistance to the Fireblight disease and its tolerance of the Pear Decline disease. It is hardy, early bearing, and has demonstrated good root-anchorage in all orchard sites where tested.

4 Drawing Figures

SUMMARY OF THE INVENTION

The original plant of this new variety was a member of a family of over 2000 pear seedlings which germinated from seed obtained from the Canadian Department of Agriculture Research Unit located near Summerland, British Columbia, Canada. This seed, collected from open-pollinated Old Home pear trees (*Pyrus communis*) which were growing in an isolated experimental planting with Farmingdale pollinizers, was planted by the inventor in his nursery at Forest Grove, Oreg. in 1952.

Experimental objectives were to develop, by trial and selection, a series of clonal pear rootstocks which would fulfill several urgent needs of both the orchardist and the nurseryman. The most important and immediate needs were for rootstocks that are resistant to Fireblight (*Erwinia amylovora*) a common, debilitating bacterial disease of pear trees. Also needed were rootstocks that are tolerant of the more recently described and equally destructive disease of pear known as Pear Decline which is a virus-like, mycoplasma-caused disorder affecting pear phloem sieve tubes below the graft union.

Another experimental objective was to select from this seedling population, rootstock clones which would root readily by vegative means. The most major additional objective was to determine and select a series of growth-controlling rootstock clones which would permit orchardists to develop plantings using tree spacing techniques tailored to known uniform tree sizes.

Old Home × Farmingdale #40 has shown its usefulness by exhibiting the following charcteristics which fulfill all of the original desired objectives. It has been chosen as the best of several "dwarfing" selections after nearly 30 years of orchard and nursery testing and evaluation.

Final selection was made in 1982 following tests which consisted of trial plantings and nursery evaluations which were carried out at Hood River, Salem, Medford, Corvallis, Dayton and Forest Grove, Oreg. and Yakima, Wash.

TEST AND EVALUATION RESULTS

1. Pear varieties grown on the rootstock of this variety are approximately 65% of the size of like pear trees grown on the most commonly used commercial pear rootstocks used in the trade. These are seedling rootstocks grown from Domestic Bartlett seed also known as Domestic pear seedlings (*Pyrus communis*). Trees grown on Bartlett seedling rootstocks are considered "standard" in size when established in the orchard and are used as the basis for all of the comparisons and measurements herein.

2. Rootstocks of this new variety are almost completely resistant to Fireblight infection whereas domestic Bartlett seedling rootstocks are shown to be highly susceptible.

3. This new clonal rootstock is believed to be Pear Decline tolerant. No Pear Decline symptoms were noted on trees grafted to this rootstock throughout the many years of testing and evaluation in the several plots where tests were conducted. In comparison, Decline symptoms were noted on trees grafted to Domestic Bartlett seedlings as well as on trees grafted to several other seedling rootstock types being evaluated.

4. The new pear rootstock clone has been virus-indexed and found to be free of all known virus diseases of pear.

5. No rootsuckering was observed on trees grafted to Old Home × Farmingdale #40 during many years of orchard trials.

6. Yield efficiency (comparing yield to unit of tree size) was rated about 6% above that of trees on Domestic Bartlett seedling rootstocks.

7. Uniformity of trees size was one of the most outstanding qualities shown by the new rootstock clone. This it is believed was at least partially due to its disease resistance in the orchard and its excellent and uniform rooting habits.

8. Young Bartlett trees propagated on the new rootstock variety have come into bearing at an earlier age than similar trees grafted on Domestic seedling stocks. Many Bartlett test trees grafted on Old Home × Farmingdale #40 bloomed heavily and set fruit during their third growing season. This was compared to Bartlett trees on seedling stocks with light sporadic sets of fruit in their fourth growing season.

9. This rootstock selection is hardy in all areas where it was tested and is considered to be hardy wherever pears are grown.

10. The new rootstock is graft-compatible with all major commercially grown pear varieties.

11. Pear trees grown on this selection show very good root-anchorage in the nursery and in the orchard.

12. Pear rootstock trees of the Old Home × Farmingdale #40 variety can be easily propagated by hardwood and softwood cuttings and/or by micropropagation methods (meristematic tissue culture). Such asexual reproductions have demonstrated that its distinctive characteristics and particularly including its "dwarfing" character are stable and are transmitted without change through succeeding propagations and generations.

GENERAL AND DETAILED DESCRIPTION

Since Old Home × Farmingdale #40 is a variety intended to be used only as a rootstock for pear cultivars, the main detailed description and accompanying drawings will center on the vegetative parts rather than the flowers and fruits. This pear selection will be propagated only asexually rather than by seed, in order to maintain its clone characteristics. The accompanying pictures show typical specimens of this new clonal pear rootstock.

FIG. 1

This picture shows a one-year old shoot of Old Home × Farmingdale #40 taken from the cuttingbed showing its straight, upright and branchless habit of growth.

FIG. 2

This picture shows typical leaves of Old Home × Farmingdale #40 showing their broad-ovate shape and finely-serrated margins. The rather short, stubby petioles are shown here with the long slender stipules at the base.

FIG. 3

This picture shows typical growth of Old Home × Farmingdale #40 in the nursery cuttingbed.

FIG. 4

This picture shows a rooted hardwood cutting of Old Home × Farmingdale #40 taken from the cuttingbed showing typical root development at the basal cut.

DESCRIPTION OF VEGETATIVE CHARACTERISTICS

The following is a detailed description of the new pear rootstock's growth characteristics as observed on one year old shoots produced from hardwood cuttings which were grown in a cuttingbed located in the propagation mursery at Forest Grove, Oreg. These observations were made during the late growing season after vigorous spring and summer growth had ceased but prior to fall leaf senescence. The new variety was also observed closely outdoors in the late fall during digging operations and again later in the tree storage warehouse where all stocks were evaluated for rooting characters prior to grading and storage. The characteristics described are those most often seen and used in the identification of a clonally propagated rootstock.

Colors of leaves and shoots herein described are based on their appearance at the site where stocks were grown, dug and stored. In those instances where a precise color assessment can be made reference is to a Munsell Limit Color Cascade chart. In other instances, general color terms are used in accordance with their ordinary dictionary significance.

General habit:
- *Strength of growth.*—Vigorous, flexible, slender.
- *Habit.*—Upright.
- *Branching.*—Thin, flexible, almost branchless.

Wood—Summer:
- *Color.*—Green (22-11) on upper side, dark-green (22-13) on lower side.
- *Pubescence.*—None.
- *Texture.*—Smooth.

Wood—Winter:
- *Stoutness.*—Willowy, flexible.
- *Diameter of shoots.*—$\frac{1}{4}''$ between buds, 5/16" across buds, 5/16" through buds.
- *Flexibility.*—Flexible.
- *Internodes.*—$1\frac{5}{8}''$, long.
- *Color.*—Olive-green (23-12) on upper side, brownish-green (23-14) on lower side.
- *Pubescence.*—None.
- *Texture.*—Smooth.

Lenticels:
- *Number.*—Few.
- *Conspicuousness.*—Summer conspicuous.
- *Shape.*—Round, slightly raised.
- *Color.*—Whitish, turning to yellow-brown (27-9).
- *Distribution.*—Scattered.
- *Size.*—Medium.

Leaves:
- *Size.*—Medium, length $2\frac{1}{2}''$, breadth $1\frac{5}{8}''$.
- *Shape.*—Broad-elliptic, ovate.
- *Base.*—Obtuse, attenuated.
- *Apex.*—Mucronate, sometimes twisted.
- *Serrations.*—Finely-serrate.
- *Surface.*—Flat, shiny, few hairs along veins and midrib.
- *Margin.*—Folded upward.
- *Pose in relation to stem.*—Erect.
- *Color.*—Green (20-14) on upper surface, green (21-12) on lower surface.
- *Pubescence.*—Few hairs along veins and midrib on upper surface, none on lower surface.
- *Texture.*—Pliant, smooth.
- *Color of tips of shoots.*—Pale yellowish-green (23-8) when still actively growing.

Petiole:
- *Pubescence.*—Slight on upper surface, none on lower surface.
- *Shape.*—Short, stubby, slightly channeled.
- *Length.*—Short, $\frac{3}{8}''$.
- *Color.*—Green (22-11), yellowish-green on new growth.
- *Pose.*—Erect.
- *Glands.*—Usually none, sometimes aborted.

Stiples (not always present):
- *Size.*—Small.
- *Margin.*—Smooth.
- *Shape.*—Long, narrow, slender.

*Length.*—7/16".
*Color.*—Light-green (21-12).
*Pose.*—Mostly reposed along petiole.

Buds:
*Size.*—Small.
*Shape.*—Short, conical.
*Color.*—Dark-brown, waxy.
*Pubescence.*—None.
*Pose.*—Somewhat appressed.

FLOWER AND FRUIT CHARACTERS

Flowers:
*Size.*—$1\frac{3}{8}$" across, average 7 buds per cluster.
*Color.*—White, occasionally tinged with pink.
*Pedicels.*—$\frac{3}{4}$" Long, slender, thinly pubescent.

Fruit (no commercial value but useful for identification):
*Size.*—$2\frac{1}{8}$ Long, $2\frac{1}{8}$" wide.
*Color.*—Yellow (26-5).
*Stem.*—Long, very thick.
*Shape.*—Wide, turbinate, inclined to truncate.

GENERAL CHARACTERISTICS

Rootsuckering: None

Size control potential: "Dwarf", about 65% of standard, less vigorous varieties more reduced in size.

Yield efficiency: Average about 6% above trees on Domestic seedling stocks. *Pyrus communis*).

Compatability: Graft-compatible with all major commercial fruiting varieties.

Rooting: Hardwood cuttings root well, roots arise mostly at basal cuts.

Root anchorage: Good in all soil types tested.

Hardiness: Hardy wherever pears are grown.

Disease resistance: Highly resistant to Fireblight (*Erwinia amylovora*), tolerant of the Pear Decliner mycoplasma organism, index tested and shown to be free of known pear viruses.

Pest resistance: Average resistance to common pests of year.

Early bearing ability: Blooms heavily and sets fruit during 3rd growing season.

I claim:

1. A new and distinctive variety of pear tree referred to by the cultivar designation Old Home × Farmingdale #40 and substantially as herein shown and described characterized particularly by its ability to serve as a size-controlling rootstock for grafting of pear tree cultivars to produce "dwarf" pear trees; further characterized by its resistance to the Fireblight disease and its tolerance of the Pear Decline disease; further characterized by its non-rootsuckering habit, its hardiness, its good root-anchorage, its good graft-compatibility with all major commercial pear varieties, its early bearing habit, and its ability to root easily and reproduce readily by hard and softwood cuttings.

* * * * *